(12) United States Patent
White et al.

(10) Patent No.: US 10,004,483 B2
(45) Date of Patent: Jun. 26, 2018

(54) SCOOP CANNULA FOR A CORING BIOPSY DEVICE

(71) Applicant: Pave, LLC, Indianapolis, IN (US)

(72) Inventors: Kimberly White, Plainfield, IN (US); Douglas Perianu Knoll, Indianapolis, IN (US); Deborah Rae Beck, Zionsville, IN (US)

(73) Assignee: Pave, LLC, Indianapolis, IN (US)

( * ) Notice: Subject to any disclaimer, the term of this patent is extended or adjusted under 35 U.S.C. 154(b) by 0 days. days.

(21) Appl. No.: 15/462,824

(22) Filed: Mar. 18, 2017

(65) Prior Publication Data

US 2017/0231606 A1    Aug. 17, 2017

Related U.S. Application Data

(63) Continuation-in-part of application No. 14/051,595, filed on Oct. 11, 2013, now abandoned.

(60) Provisional application No. 61/712,441, filed on Oct. 11, 2012.

(51) Int. Cl.
| | |
|---|---|
| *A61M 5/178* | (2006.01) |
| *A61B 10/00* | (2006.01) |
| *A61B 10/02* | (2006.01) |
| *A61B 10/06* | (2006.01) |

(52) U.S. Cl.
CPC .......... *A61B 10/0266* (2013.01); *A61B 10/06* (2013.01)

(58) Field of Classification Search
CPC .. A61B 19/54; A61B 2019/5466; A61B 10/04
USPC ......... 600/562, 564, 565, 566, 567; 604/158
See application file for complete search history.

(56) References Cited

U.S. PATENT DOCUMENTS

| | | | |
|---|---|---|---|
| 4,781,198 A | 11/1988 | Kanabrocki | |
| 5,526,822 A | 6/1996 | Burbank et al. | |
| 5,795,308 A | 8/1998 | Russin | |
| 6,050,954 A | 4/2000 | Mittermeier | |
| 7,877,133 B2 | 1/2011 | Burbank et al. | |
| 8,292,824 B2 | 10/2012 | Okada | |
| 8,454,530 B2 | 6/2013 | Nakata | |
| 8,574,167 B2 * | 11/2013 | Smith | A61B 10/0275 600/562 |
| 8,740,811 B2 * | 6/2014 | Fortems | A61B 10/025 600/566 |
| 2002/0058882 A1 | 5/2002 | Fulton, III et al. | |
| 2005/0049489 A1 | 3/2005 | Foerster et al. | |
| 2006/0030785 A1 | 2/2006 | Field et al. | |
| 2006/0167416 A1 | 7/2006 | Mathis et al. | |
| 2007/0016067 A1 | 1/2007 | Webster, III et al. | |
| 2007/0135711 A1 | 6/2007 | Chernomorsky et al. | |

(Continued)

*Primary Examiner* — May Abouelela
(74) *Attorney, Agent, or Firm* — Maginot, Moore & Beck, LLP

(57) ABSTRACT

A full-core biopsy device comprises an outer cannula hub with an outer cannula coupled at a proximal end to the hub, the outer cannula with a tissue slicing feature defined at the distal tip configured for cutting tissue. The device further comprises an inner member hub and an inner member coaxially disposed within the outer cannula and coupled at a proximal end to the inner member hub. The inner member includes a tubular body, an inner member tip at an opposite distal end thereof and an elongated scoop portion defined between the tubular body and tip. The distal ends of the outer cannula and the scoop portion of the inner member define cooperating forcing cone features.

15 Claims, 15 Drawing Sheets

(56) References Cited

U.S. PATENT DOCUMENTS

| | | |
|---|---|---|
| 2008/0221479 A1 | 9/2008 | Ritchie et al. |
| 2009/0105608 A1* | 4/2009 | Chiu .................... A61B 10/06 600/564 |
| 2009/0156961 A1 | 6/2009 | Tsonton et al. |
| 2010/0249647 A1 | 9/2010 | Nakayama |

* cited by examiner

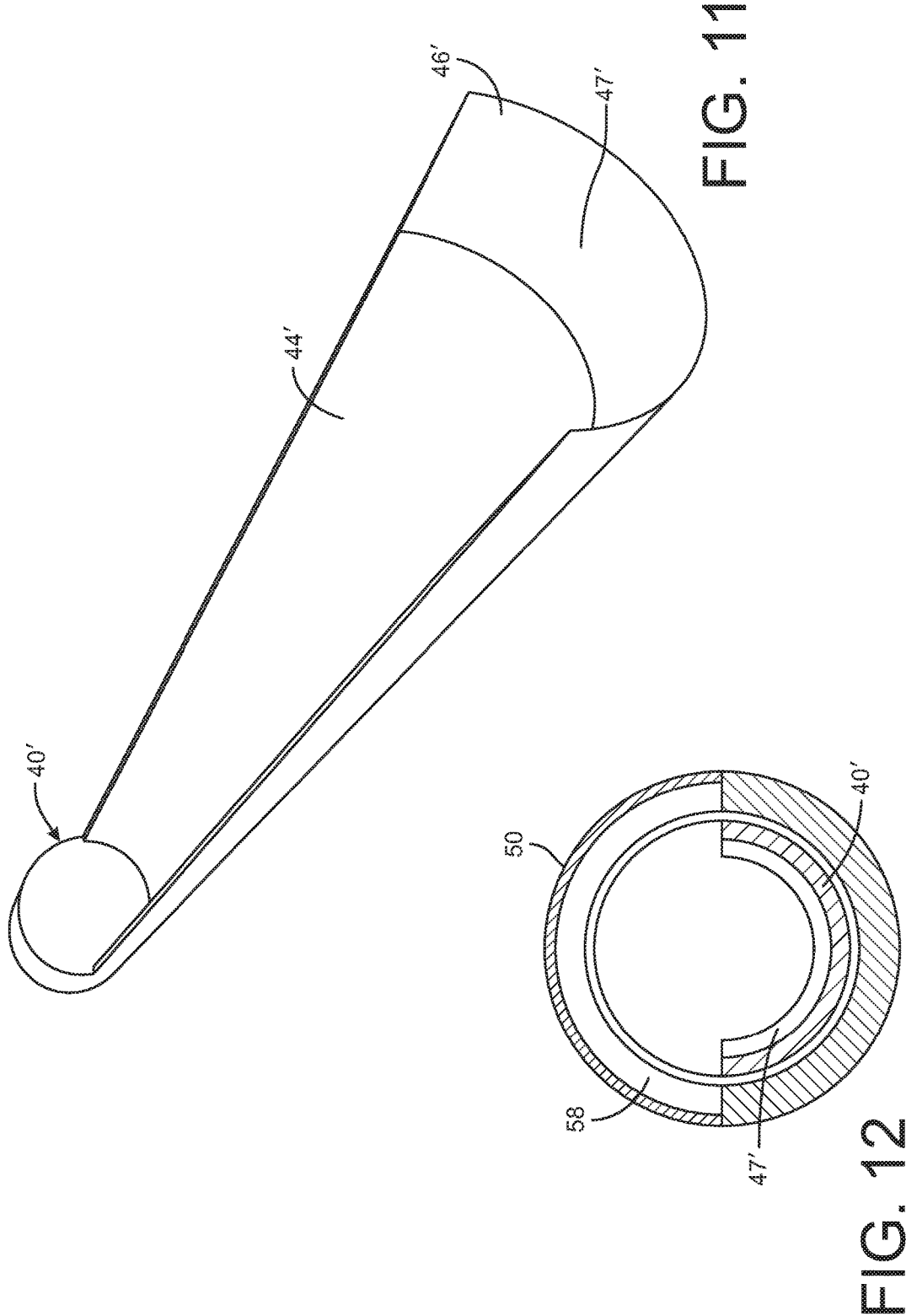

SCOOP CANNULA FOR A CORING BIOPSY DEVICE

REFERENCE TO RELATED APPLICATION

This application is a continuation-in-part of and claims priority to U.S. application Ser. No. 14/051,595, filed on Oct. 11, 2013, which is a non-provisional of and claims priority to provisional application No. 61/712,441, filed on Oct. 11, 2012 and entitled "Biopsy Device Improvements", the entire disclosures of which are incorporated herein by reference.

BACKGROUND

The present disclosure relates to biopsy devices and particularly to core biopsy devices.

A standard single action biopsy device has an outer cannula needle coaxially disposed over an inner stylet needle. The inner stylet defines a specimen notch near the distal end. The outer cannula and inner stylet are each attached to hubs and the hubs are moveable between three positions via a spring activated mechanism. The first position is a fired or neutral position. The proximal ends of the needles, the spring and carriages are housed within a casing including a handle. A plunger is engaged to the carriages. In use, the plunger is pulled back to charge the device. In the charged condition, the carriages and needles have been pulled back into the casing. When the device is charged the plunger is moveable between back and forward positions. In the forward position, the stylet has been moved forward relative to the outer cannula to expose the notch. Depressing the plunger further fires the device by releasing the outer needle carriage so that the outer needle quickly moves forward to cover the notch and sever tissue to capture a specimen within the notch.

In a single action Device, the inner stylet with the notch is manually moved with the plunger. In a double action device, both the inner stylet and outer cannula are fired automatically in rapid succession once the trigger is depressed. One advantage of a single action device over a double action device is that manual movement of the inner stylet allows the clinician to directly visualize how far the outer cannula will core tissue by noting the location of the distal point of the inner stylet. This allows the clinician to avoid coring vital structures. Some clinicians also can feel the difference between target or safe tissue and vital structures by manually moving the inner stylet with the plunger. The resistance of such tissue against movement of the stylet tip provides different tactile feedback. Using a double action device, on the other hand requires the clinician to measure the length of the throw to estimate whether the device will core a vital structure.

Both single action and double action devices reliably deliver core specimens, but they are limited in regard to the amount of tissue specimen by the dimensions of the notch. The BioPince™ device of Argon Medical Devices, Inc., was a major advancement in the field of biopsy because it provided a full rounded core, which was much larger than the specimens delivered by the "side notch" in the stylet of the single action and double action devices. While a major contribution, the BioPince had a relatively large casing and complicated mechanism.

The DEX360 Full Core Biopsy device of Promex Technologies, Inc., utilized forcing cone technology to deliver a large rounded full core with a simple, elegant mechanism. While the full core performance of both the BioPince and the DEX360 devices deliver clinically significant better cores, both devices operate like double action devices in that the clinician must measure the throw before firing.

The current invention combines the benefit of manual advancement of the inner member before coring of a single action with the forcing cone feature of a DEX360. When the plunger is advanced, a scoop portion defined in the inner needle is extended for tissue prolapse. The forcing cone in the outer cannula in combination with the scoop captures a rounded core. In some embodiments, the distal end of the scoop includes a sharpened tip, a partial forcing cone or a solid tip. For the present disclosure certain aspect of these improvements are described for use with a full-core biopsy device, such as the device described in U.S. Pat. No. 9,332,970, which was filed on Sep. 13, 2012 and issued on May 10, 2016, pending application Ser. No. 13/190,808, filed on Jul. 26, 2011, and U.S. Pat. No. 9,237,883 which was filed on Dec. 16, 2010, and issued on Jan. 19, 2016, all of which are entitled "Full Core Biopsy Device". The descriptions of the full core biopsy devices in these applications are incorporated herein by reference, but for the purposes of the present application certain features of the disclosed devices will be described herein.

One type of core biopsy device 10 is shown in FIG. 1. The device 10 includes a housing 12 that defines finger handles 14 to be grasped by the clinician during a biopsy procedure. The device can include an outer cannula or cannula 20 and an inner member 30, which may be a stylet, needle or cannula, coaxially extending through the outer cannula 20. The biopsy device 10 incorporates a mechanism for charging and firing the outer cannula relative to the inner member in order to capture a tissue sample. One embodiment of a firing mechanism is incorporated into the SABD™ product and is described in the above-referenced pending applications. In general terms, the mechanism includes carriages that carry the outer cannula and inner member, and a spring arrangement that extends the outer cannula beyond the inner member so that tissue is drawn into and trapped in the tip 26 of the outer cannula. It is noted that this outer-inner cannula relationship is not utilized in the SABD, the inner cannula is extended so tissue can prolapse into the cannula before the outer cannula fires over the inner. In is noted that the scoop cannula of the present disclosure operates in the same manner to accept tissue prolapsed into the scoop portion.

The mechanism of the full core device includes latch arrangements that allow the biopsy device to be placed in a charged configuration in which the tip 26 of the outer cannula is retracted, and then allow the device to be fired. A plunger 32 may be used to manually charge and fire the biopsy device. It should be appreciated, however, that the components described herein may be used in other types of biopsy devices, such as fully automated or double action devices.

According to one aspect, the tip 26 of the outer cannula 20 is provided with a tissue penetrating tip. In one specific aspect the tissue penetrating tip is formed as a Franseen tip, as shown in FIG. 2, having three or more prongs 27 with sharp cutting edges that permit smooth piercing of the soft tissue as the outer cannula 20 initially advances into the tissue and that provide solid purchase once the outer cannula has been fully advanced. The prongs 27 are configured to advance through the tissue without substantially compressing the tissue. The angled edge surfaces of the prongs 27 act as guillotine cutters to slice cleanly through the tissue as the outer cannula 20 advances. The distal portion of the outer cannula forms a tissue specimen chamber.

In another aspect, the distal portion of the tissue specimen chamber defines a tissue retention feature in the form of a countersink or forcing cone 28 defined in the inner surface to a depth 29 that is proximal from the valleys of the Franseen tip 26. The forcing cone has a larger inner diameter than the proximal portion of the tissue specimen chamber. The forcing cone 28 essentially "forces" or squeezes a larger diameter of tissue into the relatively smaller diameter of the tissue specimen chamber of the outer cannula beyond the forcing cone as it is advanced into the tissue, which allows for a larger diameter sample and holds the sample in place as the device is withdrawn from the biopsy site. Employing a forcing cone for the tissue retention feature allows for the entire inner diameter of the outer cannula to be available as the tissue specimen chamber. It is believed that the force of the tissue against the sidewall of the outer cannula is greater than the force folding the cells together at the end of the specimen. Therefore when the needle is withdrawn, the tissue separates at a natural plane making any other tissue separation or retention means redundant. The forcing cone 28 may be incorporated into the outer cannula of different types of biopsy devices, including side notch devices, single or double action devices and coring devices.

In the charged configuration or position of the biopsy device, the inner member 30 is situated within the outer cannula 20 so that the tip 36 preferably does not extend beyond, or extends only minimally beyond, the base of the valleys of the Franseen tip 26, as illustrated in FIG. 3. It can be appreciated that in the charged position shown in FIG. 3, the inner member hub 32 is in position to fire the device 10.

SUMMARY

In one aspect of the present disclosure, a full core biopsy device comprises an outer cannula hub with an outer cannula coupled at a proximal end to the hub, the outer cannula having a tissue slicing feature defined at the distal tip configured for cutting tissue. The outer cannula includes an angled inner surface at the tip configured to improve tissue draw into the outer cannula when the device is activated. The device further comprises an inner member hub and an inner member coaxially disposed within the outer cannula and coupled at a proximal end to the inner member hub. The device includes a firing mechanism that is operable to advance the outer cannula relative to the inner member to obtain a full core tissue sample.

In a further aspect, the inner member includes a cylindrical body, which may be solid or hollow, an inner member tip at an opposite distal end thereof and an elongated scoop portion defined between the tubular body and tip. The elongated scoop portion is partially cylindrical or subtends an angle less than 360°, and more particularly subtends an angle of about 180°. The elongated scoop portion may be sized to correspond to the stroke of the device. The distal ends of the outer cannula and the scoop portion of the inner member define cooperating forcing cone features.

DESCRIPTION OF THE FIGURES

FIG. 11 is an end perspective view of a scoop cannula incorporating a forcing cone feature, according to a further aspect of the present disclosure.

FIG. 12 is an end view of the scoop cannula of FIG. 11 incorporated into the outer cannula shown in FIG. 9.

DETAILED DESCRIPTION

Figure 1:
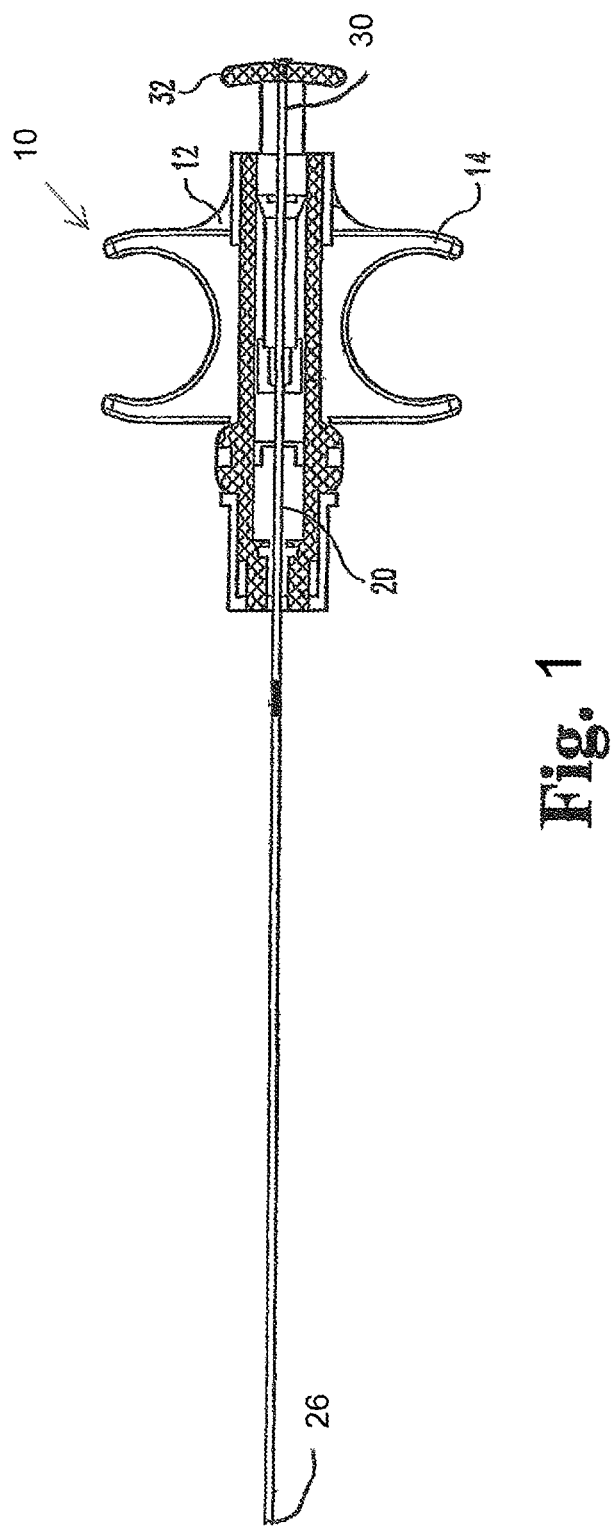
FIG. 1 is a top view of a coring biopsy device.
Figure 2:
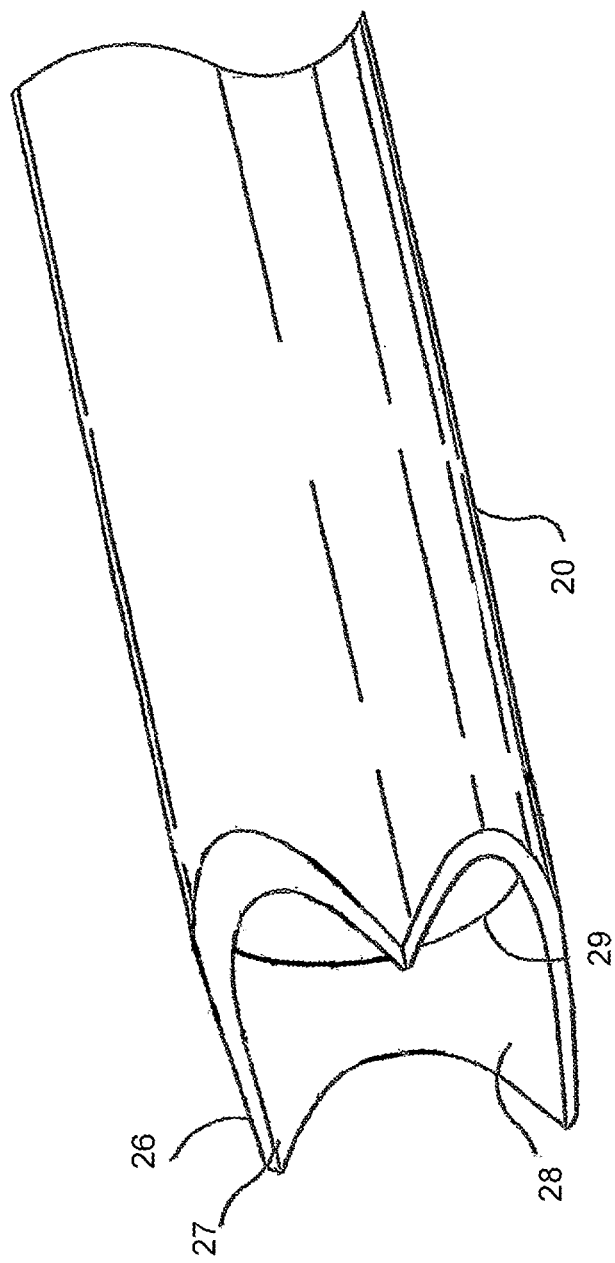
FIG. 2 is an enlarged perspective view of the cutting top of the biopsy device shown in FIG. 1.
Figure 4:
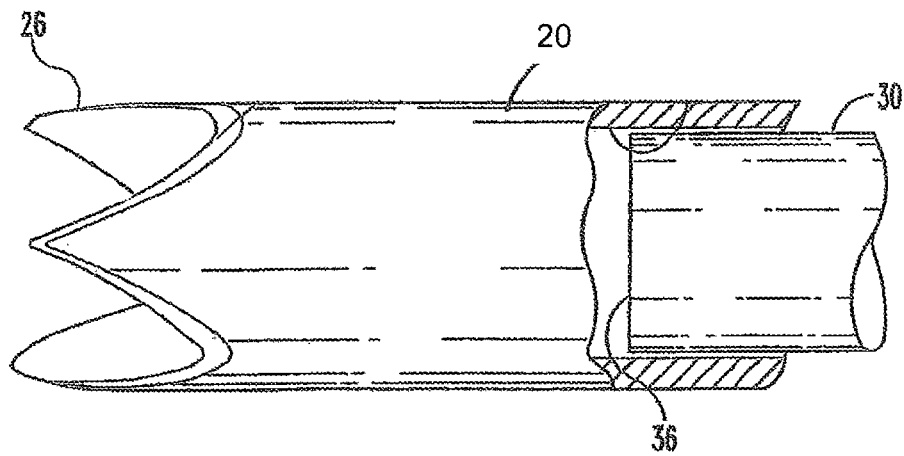
FIG. 4 is an enlarged side view of the end of the biopsy device of FIG. 1 shown with the outer cannula extended.
Figure 3:
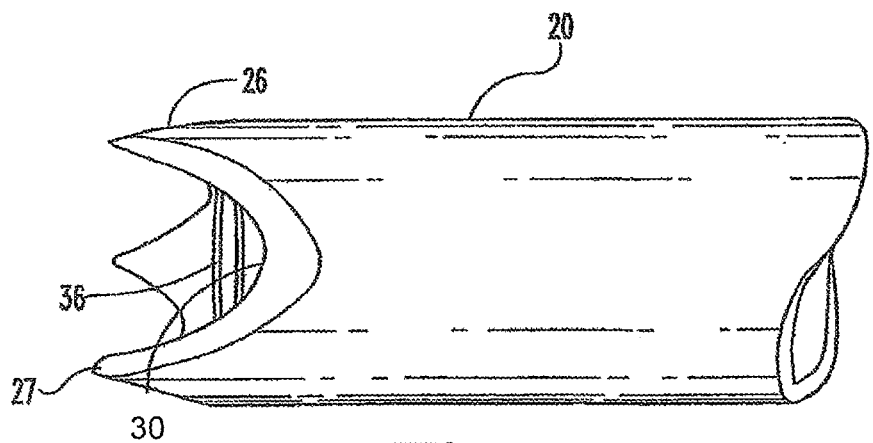
FIG. 3 is an enlarged side view of the end of the biopsy device of FIG. 1 shown with the outer cannula retracted.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 5:
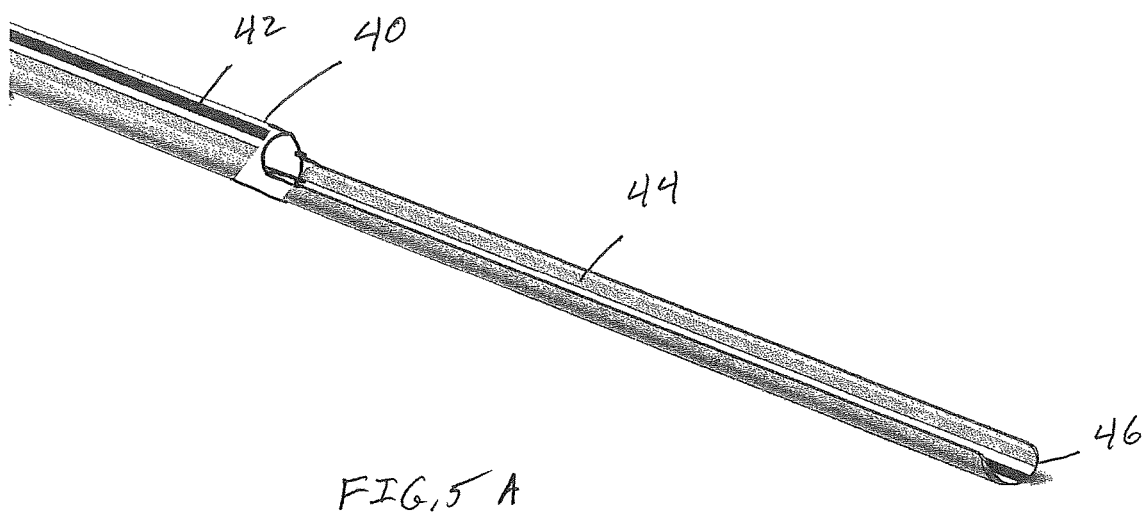
FIG. 5A is a perspective view of the end of a scoop cannula having a solid body according to one aspect of the present disclosure.
FIG. 5B is a perspective view of the end of a scoop cannula having a hollow body according to a further aspect of the present disclosure.
Figure 5:
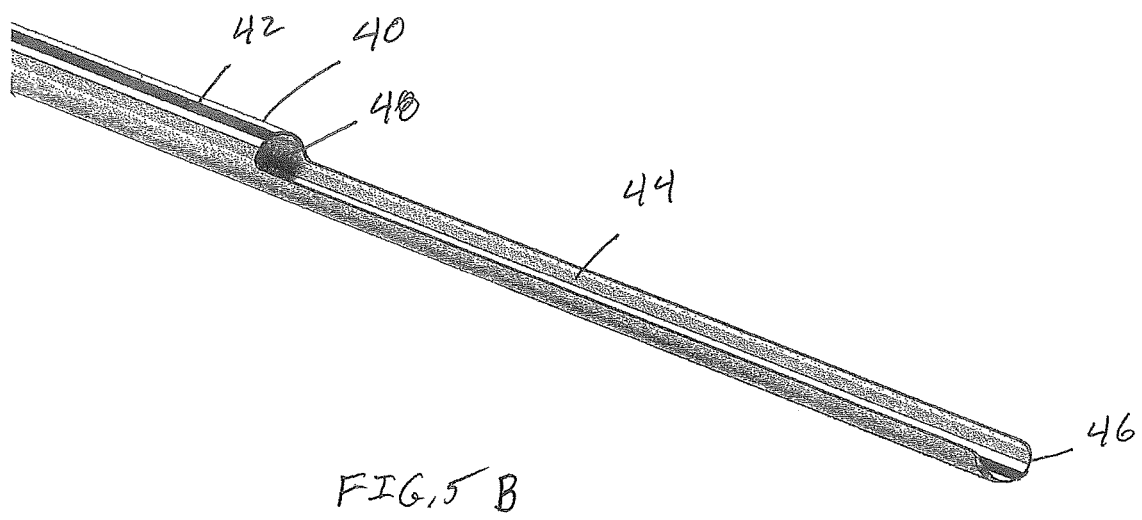

In accordance with the present disclosure, the inner stylet, needle or cannula 30 of the biopsy device 10 described above can be modified as shown in FIGS. 5-7. In particular, the biopsy device 10 may be provided with an inner member 40 that includes a main body 42. The main body may be a solid stylet or needle configuration, as shown in FIG. 5A or may constitute a tubular body defining a lumen 48 as shown in FIG. 5B. In the latter case, the lumen may be integrated with an irrigation or suction feature.

In one aspect of the present disclosure, the inner member includes a scoop portion 44 extending from the main body to a distal end 46 that is configured to penetrate tissue at the biopsy site. As seen at the distal end 46, the scoop portion 44 is defined by a partially cylindrical wall that extends for about half the circumference of the tubular body. Thus, in the illustrated embodiment the scoop portion 44 subtends an angle of about 180° to form a trough that can hold tissue. Other subtended angles are contemplated, although it is preferable that the scoop wall be configured or manufactured for sufficient rigidity and resistance to flexure as the device is introduced into a biopsy site or when the device is fired as described above.

Figure 8:
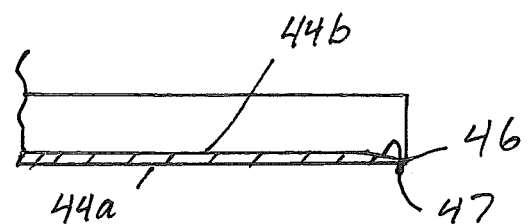
FIG. 8 is an enlarged cross-sectional view of the end of the scoop portion of the scooped cannula shown in FIGS. 5-7.

The distal end 46 of the scoop portion 44 may include a sharpened cutting edge to facilitate passage through tissue and clean slicing of the tissue as the scooped catheter is introduced into the biopsy site. In one embodiment, the sharpened cutting edge is formed at the inner surface of the cannula. In other words, the outer surface 44a of the cannula may have a constant radius throughout the entire length of the cannula, including the tubular body 42, while the inner surface 44b defines an angled surface 47 at the tip 46, as shown in FIG. 8, to produce a sharp cutting edge. The angled surface 47 may define an angle of 3-5° to facilitate introduction of tissue into the scooped cannula. In one feature, the scoop forcing cone completes the forcing cone formed by the outer cannula.

In one embodiment, the inner member 40 may be formed by performing an O.D. grind at the end of a stylet or a needle and then cutting a notch along the end of the cannula to form the scoop 44. Alternatively, the scoop 44 may be created by wire EDM on bar stock. The notch may be cut so that the scoop portion 44 has a predetermined length from the opening of the lumen 48 of the tubular body 42 to the distal end 46. This predetermined length may correspond to the stroke or throw of the outer cannula 20 when the device is fired. For example, in one specific embodiment the length of the scoop portion 44 may be about 2 cm. It is contemplated that the inner member 40 can be formed using other suitable techniques.

Figure 6:
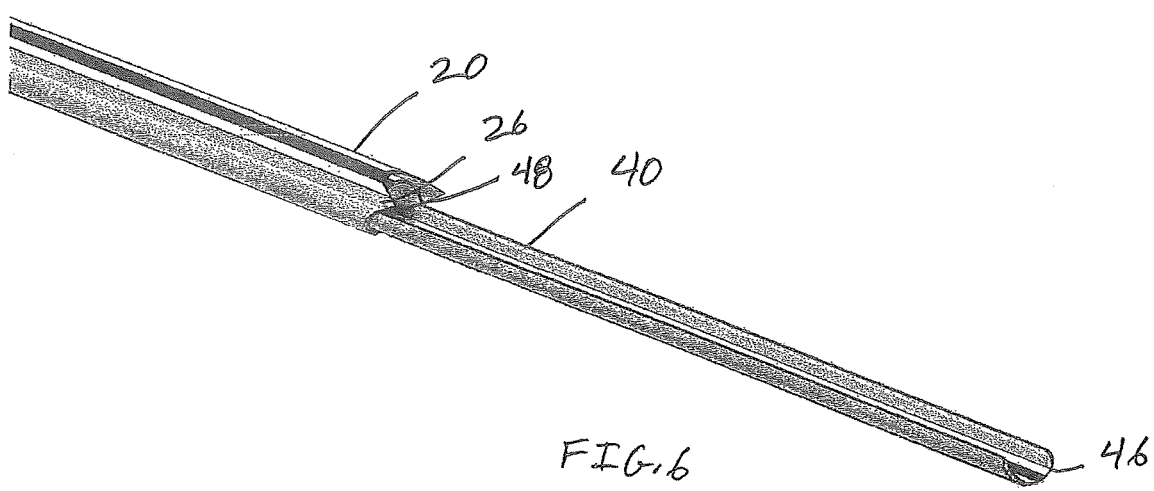
FIG. 6 is a perspective view of the scoop cannula shown in FIG. 5 incorporated into the outer cannula of the biopsy device shown in FIG. 1.
Figure 7:
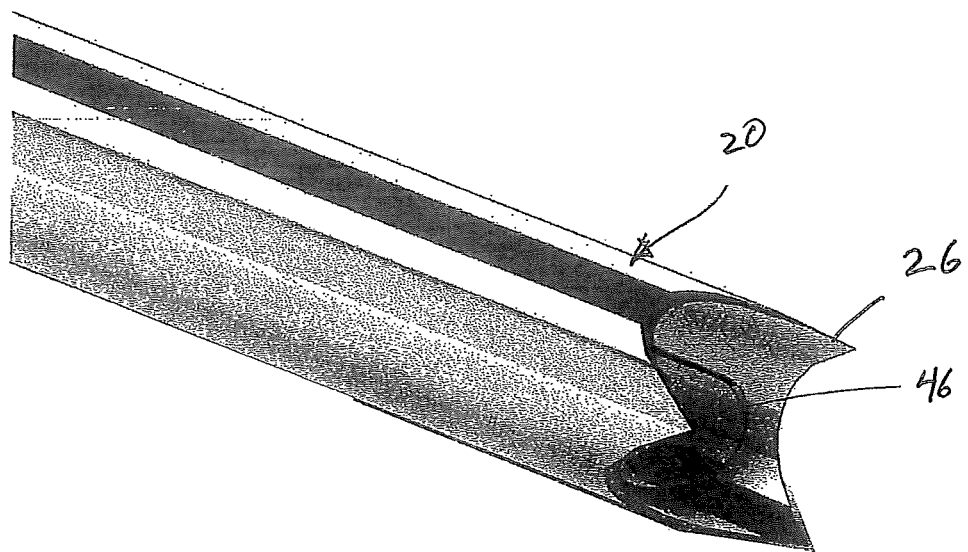
FIG. 7 is a perspective view of the scoop cannula and outer cannula shown in FIG. 6 depicted with the scoop cannula retracted within the outer cannula.

In certain uses of the device 10 it is desirable to have an indication of the extent of the outer cannula stroke when the device is introduced into a biopsy site. Thus, the scoop portion 44 may have a length approximately equal to the stroke of the biopsy device. The firing mechanism of the device may be configured to allow the inner member to be extended beyond the distal end 26 of the outer cannula in situ after the device is charged but prior to firing, as illustrated in FIG. 6. With the scooped cannula 40 extended beyond the outer cannula the inner member 40 can act as an introducer for the biopsy device and, at least initially, as an anchor for orienting the device relative to the desired biopsy site. The position of the scoop can be visualized, such as by x-ray, to provide an indication of the tissue sample that will be extracted when the device is fired. The inner member can be retracted to the position shown in FIG. 7 prior to firing the device, in the case of a double action device, or may be retained in the extended position for a single action device as the device is fired.

In other embodiments, the scoop portion 44 may be attached to or formed as part of a solid stylet to form the inner member 40. The scoop portion may be removably attached to be removed along with the tissue sample after a biopsy procedure. In further embodiments, a solid tip may be formed on or attached to the distal end 46 of the scoop portion. The solid tip may be in the form of a Trocar, a bevel, a conical "pencil point" configuration or other known tip designs.

The inner member 40 and scoop portion 44 disclosed herein are configured for passage through a full core outer cannula 20, but it is understood that the same inner member may be used with other biopsy devices, such as the SABD™ discussed above. In some uses it may be desirable to block the lumen 48 when the device is fired to prevent the tissue sample from being drawn into the inner member. In this instance a plug, such as an obturator, may be introduced into the inner member 40 prior to firing. Alternatively, the lumen can remain open and the obturator may be used to help expel the tissue sample when the device is removed from the patient.

Figure 9:
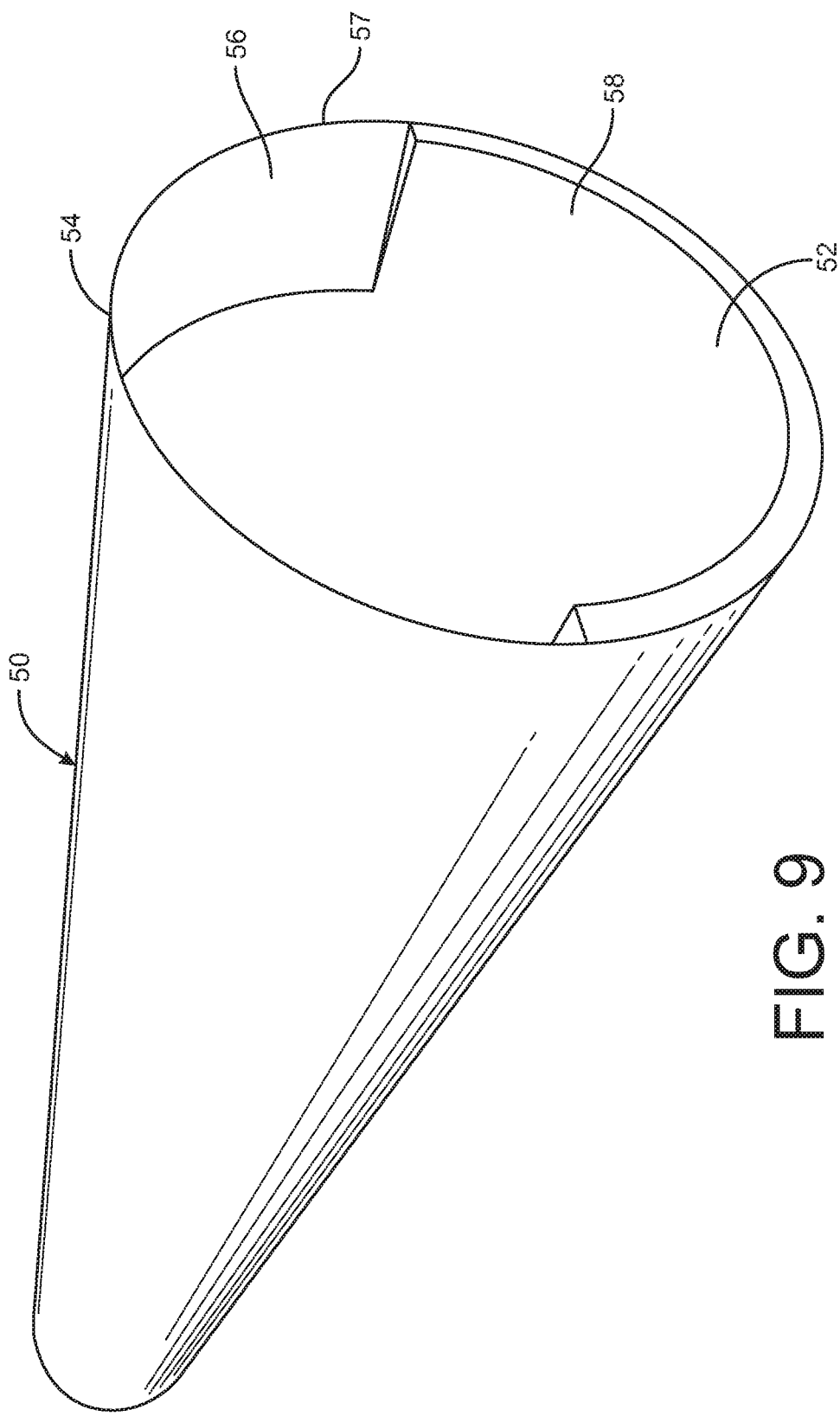
FIG. 9 is an end perspective view of an outer cannula for use with the scoop cannula shown in FIG. 5 in another aspect of the present disclosure.

In an alternative embodiment, an outer cannula 50 is provided that can be used with the inner member 40. The outer cannula, as shown in FIG. 9, includes an inner wall 52 that defines a lumen to receive the inner member 40. Whereas the distal end of the outer cannula 20 includes a countersink or forcing cone 28 that extends around the entire inner circumference at the tip of the cannula, the distal end 54 of the outer cannula 50 includes a forcing cone or countersink 56 that extends only over less than the entire inner circumference. This circumferentially truncated forcing cone can be matched with a forcing cone defined on the inner member, as discussed below. This forcing cone can also define a sharp cutting edge 57 at the distal end of the cannula. The truncated forcing cone 56 subtends a circumferential angle that is complementary to the circumferential angle subtended by the partially cylindrical wall of the inner member. Thus, if the partially cylindrical wall forming the scoop portion subtends the lower 180° of the circumference, the forcing cone 56 of the outer cannula subtends the upper 180° of the circumference.

Figure 10:
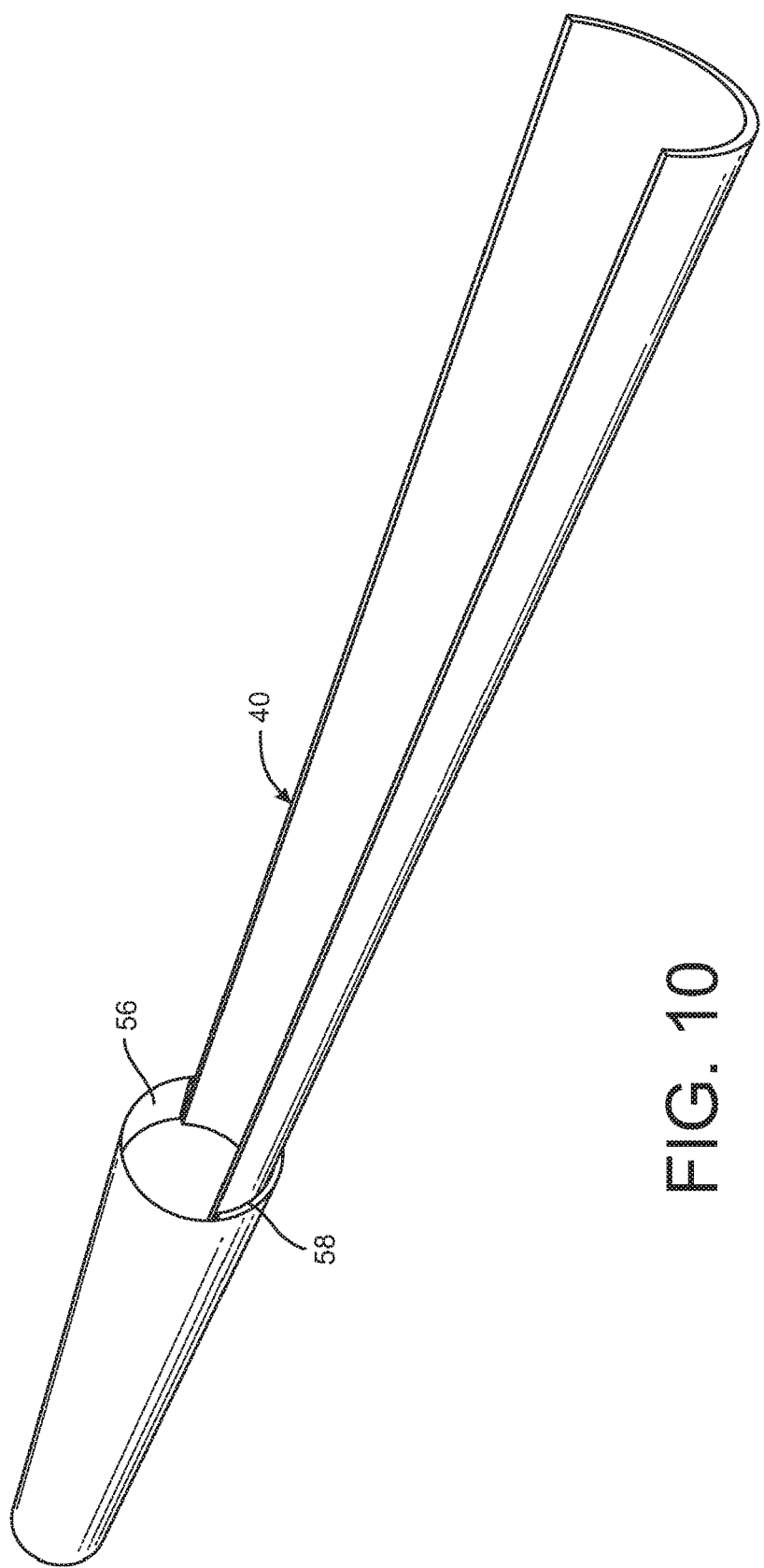
FIG. 10 is a side perspective view of the scoop cannula of FIG. 5 incorporated into the outer cannula shown in FIG. 9.
Figure 13:
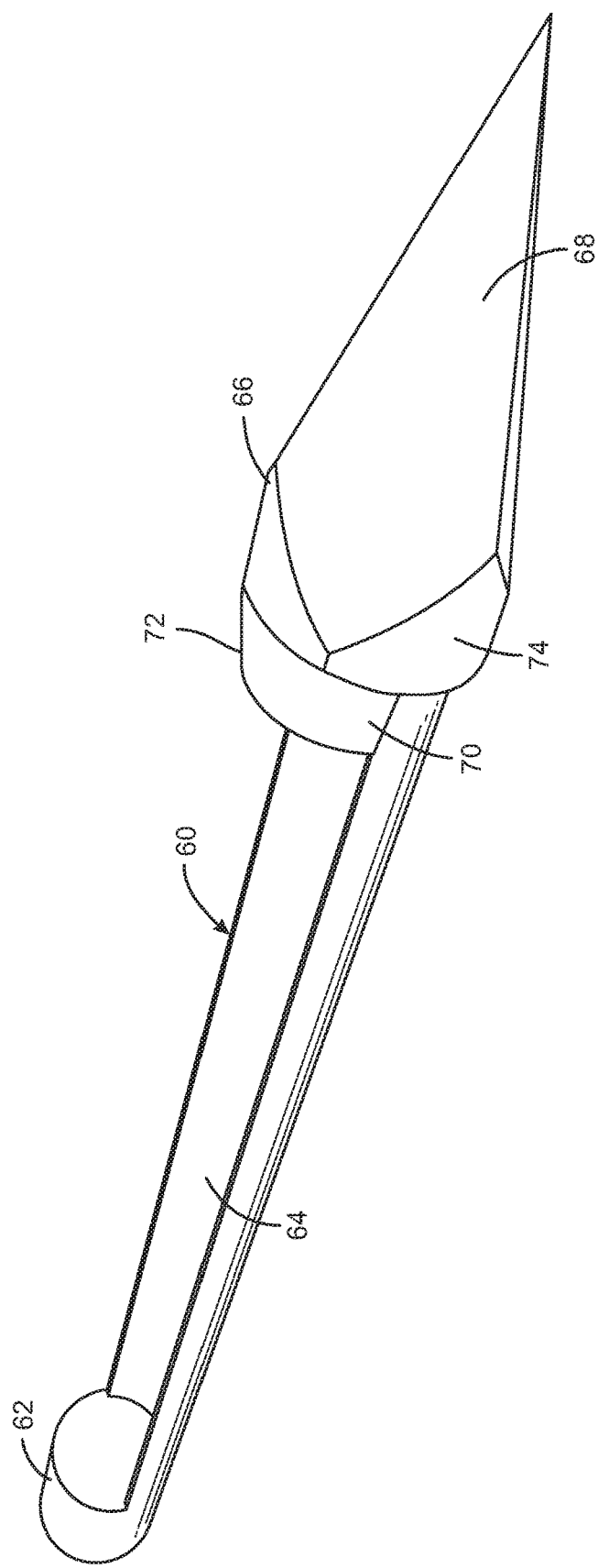
FIG. 13 is a side perspective view of an inner scoop cannula according to further aspect of the present disclosure.
Figure 14:
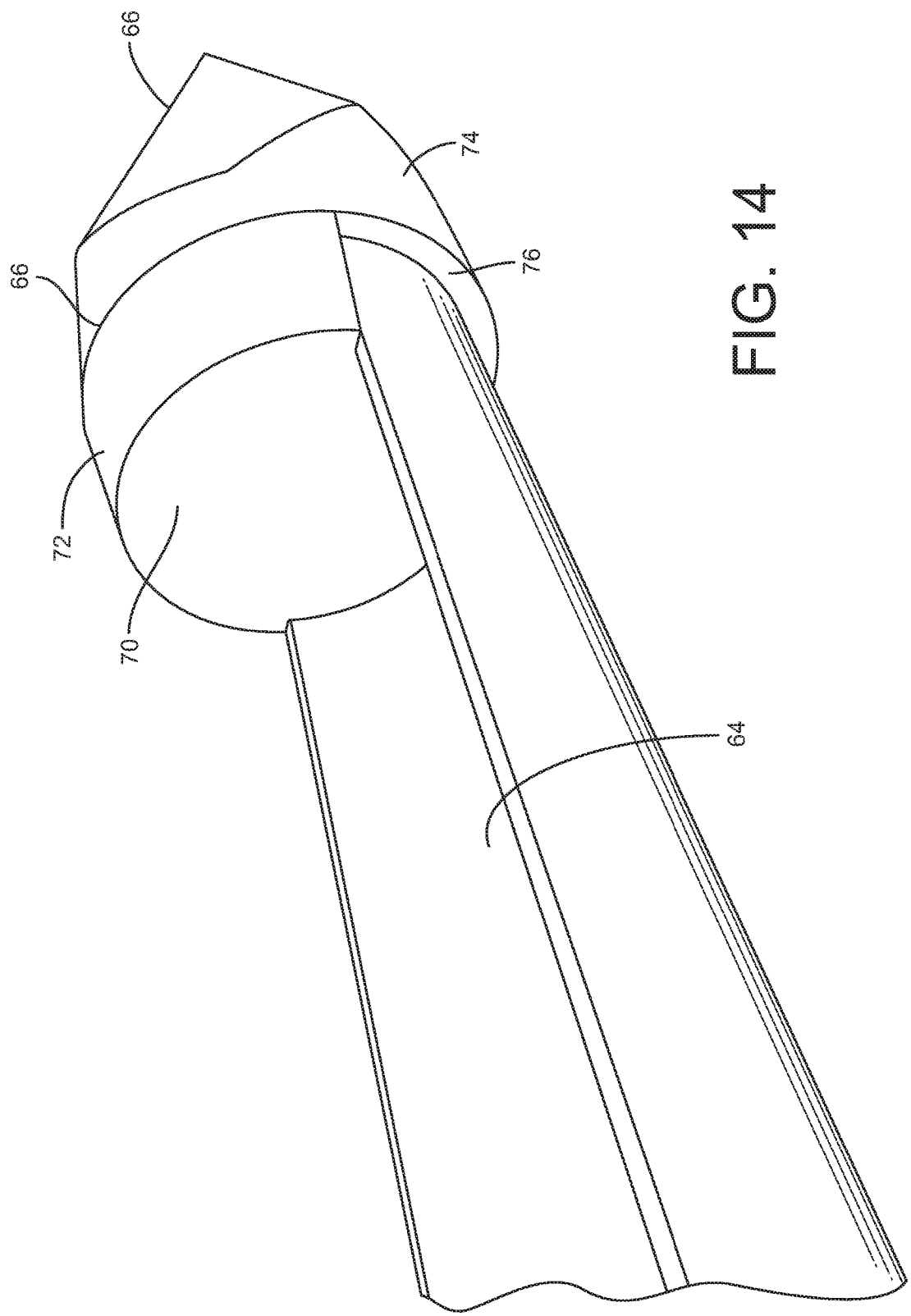
FIG. 14 is an end perspective view of the inner scoop cannula shown in FIG. 13.
Figure 15:
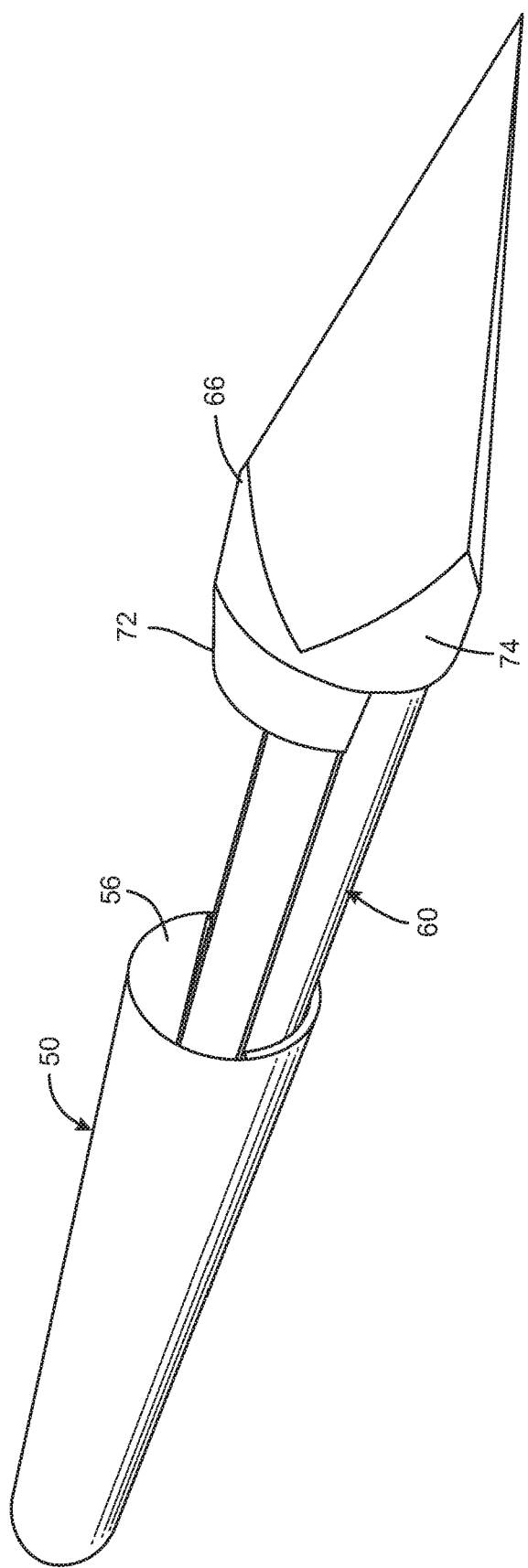
FIG. 15 is a side perspective view of the inner scoop cannula of FIG. 13 incorporated into the outer cannula of FIG. 9 shown with the inner scoop cannula in a partially extended position.
Figure 16:
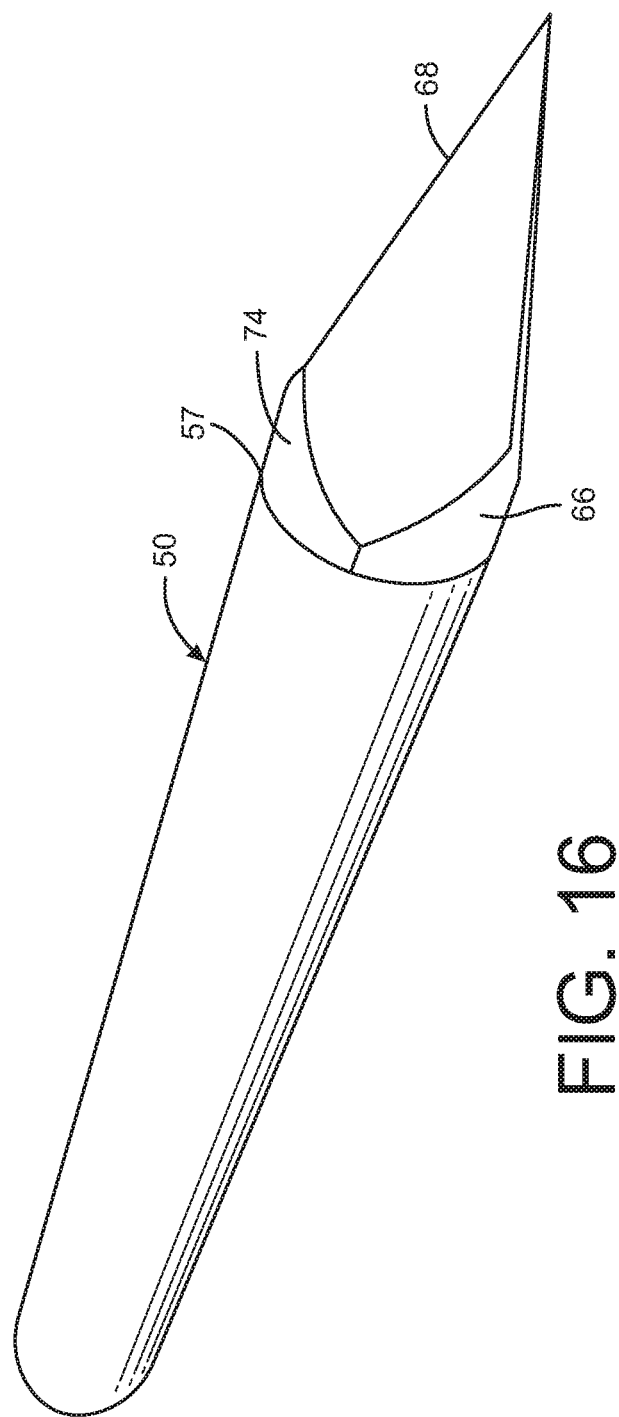
FIG. 16 is a side perspective view of the inner scoop cannula and outer cannula of FIG. 15 shown with the inner scoop cannula in its fully retracted position.
Figure 17:
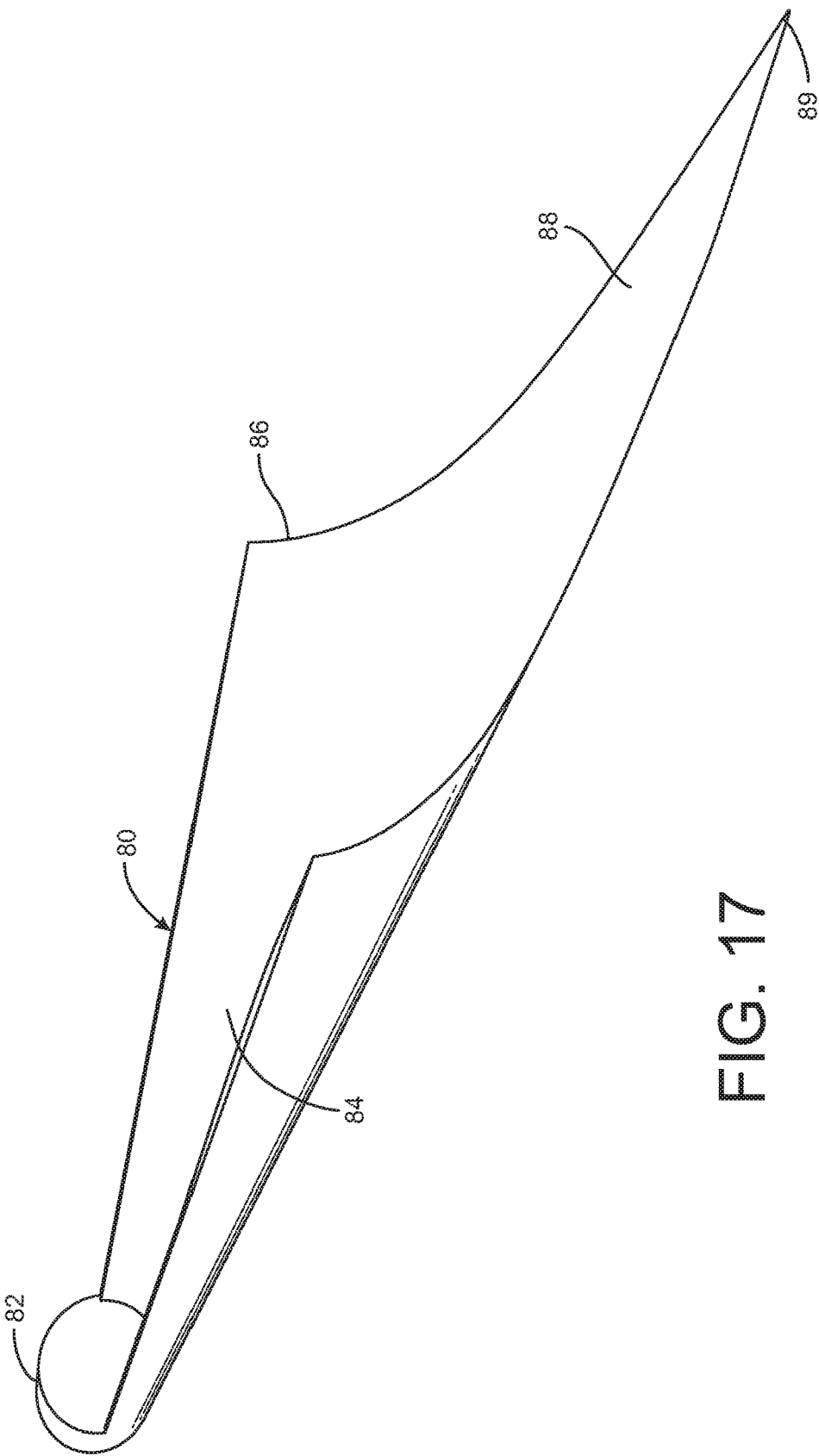
FIG. 17 is an end perspective view of the inner scoop cannula according to a further embodiment.

The remaining portion of the circumference 58 does not have any countersink and instead is formed at the same inner radius as the inner wall 52 proximal to the countersink 56. In one specific embodiment, the portion 58 without the forcing cone is co-extensive with the scoop portion 44 of the inner member 40 (FIG. 5A), as illustrated in FIG. 10. In the embodiment described above, the scoop portion 44 subtends an angle of 180°, so the portion 58 of the outer cannula 50 also subtends an angle of about 180°. It can be appreciated that the distal edge of the outer cannula is blunt at the portion 58, although the end can be beveled to form a sharpened edge. However, in this embodiment, the distal end 46 of the inner member 40 can be provided with a sharpened edge 47 (FIG. 8) to sever tissue upon introduction of the inner member, in which case the blunt edge of the portion 58 can follow the path already prepared by the inner member. On the other hand, since the upper forcing cone 56 of the outer cannula is passing through tissue that has not yet been severed, the sharpened cutting edge 57 facilitates passage of the outer cannula through the tissue. The forcing cone 56 further acts in the manner of the forcing cone 28 of the outer cannula 20 to help force tissue collected by the scoop into the outer cannula and retain that tissue within the outer cannula as the device is withdrawn from the biopsy site.

The inner member may be modified to cooperate with the forcing cone 56 of the outer member 50. In particular, a modified inner member 40', shown in FIG. 11, includes the same scoop portion 44' but the distal end 46' is modified so that the angled surface 47' is defined at an angle that matches the angle of the forcing cone 56 of the outer member. Thus, in one embodiment, the two forcing cones 56 and 47' may be defined at an angle of 1-5° and be substantially coextensive over a length of 1-5 mm (0.04-0.21 in.) to facilitate introduction of tissue into the scooped cannula. The two forcing cones cooperate, as shown in FIG. 12, to avoid any gap between the inner and outer members gap that might trap tissue In a further embodiment, an inner member 60, shown in FIGS. 11-12, includes a scoop portion 64 similar to the scoop portion 44 of the inner member 40. However, in this embodiment, the distal end 66 of the inner member 60 terminates in a sharpened tip 68. The sharpened tip 68 may be, for instance, a trocar tip, or others known in the art. The proximal end 62 of the inner member is preferably a solid body, so that the inner member 60 has the characteristics of a full core side notch device. The tip 66 is configured to readily penetrate tissue as the inner member 60 is advanced into the biopsy site. Once the inner member is in position, the surrounding tissue prolapses into the scoop portion 64, in the manner of a side notch device. The inner member 60 may be used with any of the outer cannula described above, including the outer cannula 20 and the outer cannula 50. With the tissue prolapsed into the scoop portion 64, the outer cannula is advanced toward the distal end 66 of the inner member to capture the tissue within the outer cannula.

The inner member 60 incorporates additional features to coincide with the outer cannula 50. In particular, the distal end 66 is configured to mate with the distal end of the outer cannula, and in particular with the forcing cone 56 and non-forcing cone portion 58 (FIG. 9). The distal end 66 thus includes an upper portion 70 that projects proximally from a cylindrical body 74 of the distal end. The upper portion further defines a tapered surface 72 that corresponds with the countersink or forcing cone 56 of the outer cannula. The body 74 defines an annular proximally-facing ledge 76 that is arranged to contact the edge of the non-forcing cone portion 58 of the outer cannula. Thus, the ledge 76 is contiguous with the portion 58, which in the illustrated embodiment subtends an angle of 180°. Similarly, the upper portion 70 is contiguous with the countersink or forcing cone of the outer cannula. The distal end 66 is thus configured so that the body 74 essentially fully closes the distal end of the outer needle as the upper portion 70 nests within the countersink 56. It can be appreciated that the countersink or forcing cone 56 of the outer cannula 50 performs as described above to force the tissue captured in the scoop portion into the outer cannula as the cannula is advanced toward the distal end 66 of the inner member 60.

In a further embodiment, the inner member 80 can include a proximal end 62 and scoop portion 64 similar to the previous embodiments. However, the distal end 86 of the inner member 80 is modified to a nib configuration 88. The nib configuration extends from the half-circumference of the scoop portion 84 with the circumferential extent gradually decreasing to a sharpened point 89. The distal end 88 is thus configured to be easily introduced into tissue.

The foregoing detailed description of one or more embodiments of the biopsy device with an inner member disposed within an outer cannula has been presented herein by way of example and not limitation. It will be recognized that there are advantages to certain individual features and functions described herein. Moreover, it will be recognized that various alternatives, modifications, variations or improvements of the above-disclosed embodiments and other features and functions, or alternatives thereof, may be desirably combined into many other different embodiments, systems or applications. Presently unforeseen or unanticipated alternatives, modifications, variations or improvements therein may be subsequently made by those skilled in the art which are also intended to be encompassed by the appended claims.

What is claimed is:
1. A biopsy device comprising:
an outer cannula hub;
an outer cannula coupled at a proximal end of the outer cannula hub, the outer cannula including:
an outer cannula tip at an opposite distal end;
a tissue slicing feature defined at said tip configured to cut tissue; and an inner surface including a countersink formed at said tip and extending 1.0-5.0 mm (0.04-0.21 in.) proximally from said tip beyond said tissue slicing feature;
an inner member hub; and
an inner member coupled at a proximal end of said inner member hub, said inner member including;
a main cylindrical body configured to be disposed coaxially within the outer cannula; and
a scoop portion extending from said main body and defined by a partially cylindrical wall configured to be disposed coaxially within the outer cannula.

2. The biopsy device according to claim 1, wherein said partially cylindrical wall subtends a circumferential angle of 180 degrees.

3. The biopsy device according to claim 2, wherein said countersink in said inner surface of said outer cannula subtends a circumferential angle that is complementary to the circumferential angle of said partially cylindrical wall.

4. The biopsy device according to claim 1, wherein said scoop portion includes a second distal end having a sharpened edge configured for slicing tissue.

5. The biopsy device according to claim 4, wherein said second distal end of said scoop portion has a nib configuration defining said sharpened edge.

6. The biopsy device according to claim 1, wherein said scoop portion includes a second inner surface and said second inner surface includes a second countersink at a second distal end of said scoop portion that is substantially coextensive with the countersink in said outer cannula.

7. The biopsy device according to claim 6, wherein the countersink of said outer cannula and the second countersink of said scoop portion of said inner member are defined at an angle of one to five degrees (1-5°).

8. The biopsy device according to claim 6, wherein:
said partially cylindrical wall subtends a first circumferential angle; and
said countersink in said inner surface of said outer cannula subtends a second circumferential angle that is complementary to the first circumferential angle of said partially cylindrical wall.

9. The biopsy device according to claim 1, further comprising a mechanism coupled to said outer cannula hub and said inner member hub configured to charge and fire said outer cannula relative to said inner member to capture a tissue sample within said outer cannula tip, said mechanism configured to fire said outer cannula at a stroke length relative to the inner member.

10. The biopsy device according to claim 9, wherein said scoop portion has a length from said main body that is approximately equal to said stroke length.

11. The biopsy device according to claim 1, wherein said main cylindrical body of said inner member is solid.

12. The biopsy device of claim 1, wherein said tissue slicing feature of said outer cannula is a Franseen tip.

13. The biopsy device of claim 1, wherein the inner member includes a distal end opposite said cylindrical body, said distal end including a trocar tip.

14. The biopsy device of claim 13, wherein said distal end of said inner member includes a second cylindrical body from which said trocar tip extends, said second cylindrical body including an upper portion defining a tapered surface that corresponds to and nests within said countersink in said outer cannula.

15. The biopsy device of claim 14, wherein said second cylindrical body further defines an annular proximally-facing ledge that is coextensive with the partially cylindrical wall of said scoop portion and that is arranged to contact the distal end of said outer cannula.

\* \* \* \* \*